US009682255B2

(12) United States Patent
Vahala (10) Patent No.: US 9,682,255 B2
(45) Date of Patent: Jun. 20, 2017

(54) DEVICE PRODUCING TEST SONICATIONS FOR HIGH INTENSITY FOCUSED ULTRASOUND AND METHOD OF USE

(75) Inventor: Erkki Tapani Vahala, Hyvinkaa (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 729 days.

(21) Appl. No.: 14/122,542

(22) PCT Filed: Jun. 1, 2012

(86) PCT No.: PCT/IB2012/052772
§ 371 (c)(1),
(2), (4) Date: Dec. 3, 2013

(87) PCT Pub. No.: WO2012/168840
PCT Pub. Date: Dec. 13, 2012

(65) Prior Publication Data
US 2014/0094683 A1    Apr. 3, 2014

(30) Foreign Application Priority Data
Jun. 6, 2011   (EP) .................................... 11168777

(51) Int. Cl.
*A61N 7/02*        (2006.01)
*A61B 5/055*     (2006.01)
(Continued)

(52) U.S. Cl.
CPC ................ *A61N 7/02* (2013.01); *A61B 5/055* (2013.01); *A61B 5/4836* (2013.01); *A61B 5/742* (2013.01);
(Continued)

(58) Field of Classification Search
CPC  A61B 2018/00642; A61B 2018/00678; A61B 2090/374; A61B 5/055;
(Continued)

(56) References Cited

U.S. PATENT DOCUMENTS 4,708,127 A    11/1987  Abdelghani
8,801,615 B2 *  8/2014  Fernandez ............. A61N 7/022
                                                                 600/407
(Continued)

FOREIGN PATENT DOCUMENTS

JP        H0747079 A      2/1995
WO      200232304 A1    4/2002
(Continued)

*Primary Examiner* — Ruth S Smith (57) ABSTRACT

A medical apparatus (600, 700, 800) including a high intensity focused ultrasound system (602), a signaling device (628) for generating a discomfort signal during the sonication of the sonication volume, and a processor (634) for executing instructions. Execution of the instructions causes the processor to receive (102) a set of sonication points (658, 904). At least one of the set of sonication points is identified as a test location (908, 912). The instructions further cause the processor to perform for each sonication point: determine (106) if it is a test location; perform (108) a test sonication (204, 304, 404, 504) if it is a test location; repeatedly test (110) for the discomfort signal during the test sonication; sonicate (114) the sonication point if it is not a test location or if the discomfort signal was not detected; and abort (112) the sonication if the discomfort signal was detected.

18 Claims, 6 Drawing Sheets

(51) Int. Cl.
  *A61B 5/00* (2006.01)
  *A61B 6/03* (2006.01)
  *A61B 8/13* (2006.01)
  *A61B 8/00* (2006.01)
  *A61B 18/00* (2006.01)
  *A61N 7/00* (2006.01)
  *A61B 6/00* (2006.01)
  *A61B 90/00* (2016.01)

(52) U.S. Cl.
  CPC .............. *A61B 5/748* (2013.01); *A61B 6/032* (2013.01); *A61B 8/13* (2013.01); *A61B 8/58* (2013.01); *A61B 6/506* (2013.01); *A61B 2018/00642* (2013.01); *A61B 2018/00678* (2013.01); *A61B 2090/374* (2016.02); *A61N 2007/0091* (2013.01)

(58) Field of Classification Search
  CPC ....... A61B 5/4836; A61B 5/742; A61B 5/748; A61B 6/032; A61B 6/506; A61B 8/13; A61B 8/58; A61N 2007/0091; A61N 7/02
  See application file for complete search history.

(56) References Cited

U.S. PATENT DOCUMENTS

| | | | |
|---|---|---|---|
| 8,845,559 B2* | 9/2014 | Darlington | A61N 7/02 600/437 |
| 2008/0188745 A1 | 8/2008 | Chen et al. | |
| 2008/0269847 A1 | 10/2008 | Nemenov | |
| 2009/0054772 A1 | 2/2009 | Lin et al. | |
| 2010/0036291 A1 | 2/2010 | Darlington | |
| 2010/0081893 A1 | 4/2010 | Jarvik | |
| 2011/0009734 A1 | 1/2011 | Foley | |
| 2011/0295160 A1* | 12/2011 | Hart | G06F 19/3481 601/2 |

FOREIGN PATENT DOCUMENTS

| | | |
|---|---|---|
| WO | 03009757 A1 | 2/2003 |
| WO | 2010140086 A1 | 12/2010 |

* cited by examiner

DEVICE PRODUCING TEST SONICATIONS FOR HIGH INTENSITY FOCUSED ULTRASOUND AND METHOD OF USE

CROSS-REFERENCE TO PRIOR APPLICATIONS

This application is the U.S. National Phase application under 35 U.S.C. §371 of International Application No. PCT/IB2012/052772, filed on Jun. 1, 2012, which claims the benefit of European Patent Application No. 11168777.8, filed on Jun. 6, 2011. These applications are hereby incorporated by reference herein.

TECHNICAL FIELD

The invention relates to high intensity focused ultrasound, in particular the performing test sonications before sonicating a target.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures.

To selectively treat tissue, a focused ultrasonic transducer can be used to focus the ultrasound on a particular treatment volume. The transducer is typically mounted within a medium, such as degassed water, that is able to transmit ultrasound. Actuators are then used to adjust the position of the ultrasonic transducer and thereby adjust the tissue region that is being treated.

SUMMARY OF THE INVENTION

The invention provides for a medical apparatus, a computer program product and a method of operating a medical apparatus in the independent claims. Embodiments are given in the dependent claims.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. the memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage devices. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

Medical image data is defined herein as two or three dimensional data that has been acquired using a medical imaging system. A medical imaging system is defined herein as an apparatus adapted for acquiring information about the physical structure of a subject or patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer. A magnetic resonance image is an example of medical image data.

In one aspect the invention provides for a medical apparatus comprising a high-intensity focused ultrasound system configured for generating focused ultrasonic energy for sonicating a treatment volume of a subject. The medical apparatus further comprises a signaling device configured to enable the subject to generate a discomfort signal during the sonication of the sonication volume. The signaling device may for instance be any device which the subject may use to generate a signal upon feeling a discomfort. The signaling device may for instance be an electronic device which generates a signal when a button, lever, or slide is moved or depressed. The signaling device may also be a voice recognition system which recognizes a vocal command or signal from the subject.

The medical apparatus further comprises a memory containing machine executable instructions. The machine executable instructions may for instance be executed by a processor. The medical apparatus further comprises a processor for controlling the medical apparatus. Execution of the instructions causes the processor to receive a set of sonication points. The set of sonication points contain coordinates of locations within the treatment volume. The sonication points are discreet locations within the treatment volume that are to be sonicated by the high-intensity focused ultrasound system. The high-intensity focused ultrasound system may sonicate the treatment volume by sequentially sonicating each of the set of sonication points.

At least one of the set of sonication points is identified as a test location. A test location as used herein is a sonication point at which a test sonication is performed before a normal sonication to determine if the subject will experience pain during the sonication. Execution of the instructions further causes the processor to determine if a sonication point is at a test location for each sonication point of the set of sonication points. The sonication point may be chosen from the set of sonication points. Execution of the instructions further causes the processor to control the medical apparatus to perform a test sonication of the sonication point using the high-intensity focused ultrasound system if the sonication point is the test location for each sonication point of the set of sonication points. Execution of the instructions further cause the processor to control the medical apparatus to repeatedly test for the discomfort signal from the signaling device during the test sonication. This is performed for each sonication point of the set of sonication points. Execution of the instructions further causes the processor to control the medical apparatus to sonicate the sonication point if the sonication point is not a test location or if the signal is not detected. Execution of the instructions further causes the processor to abort the sonication if the signal was detected. This and the previous step are performed for each point of the set of sonication points.

This embodiment may have the advantage that there is reduced pain to a subject during sonication of the treatment volume. This embodiment may further have the benefit that since the test sonication allows identification of sonication points which may cause pain before a full power sonication is performed that the throughput of the medical apparatus may be higher. For instance if a subject is being sonicated and the subject feels pain then the procedure for sonicating the treatment volume may have to be aborted. Using the medical apparatus as described in this embodiment this may not be the case. This is because points or sonication points which may cause the subject pain are identified before the original or full power sonication is performed using a test sonication. This may in some instances lead to a situation where a sonication point is removed from the sonication volume without causing damage to the subject.

Nerve pain of the back is a common side-effect in high intensity ultrasound treatment of uterine fibroids. One of the reasons for the pain is the ultrasound-induced pressure on the nerves. A failure to detect the pain in time leads to an aborted sonication, which in turn results in partially sonicated volumes and prolonged procedure times. Embodiments of the invention may employ low-duty-cycle, high power ultrasound pulses may be prepended to a normal sonication protocol to trigger pressure-induced back pain before the actual heating starts, allowing for fast rejection of potentially problematic sonications.

High intensity focused ultrasound (HIFU) may induce low-frequency pressure waves and a constant displacement in the tissue. When the ultrasound is directed towards sensitive structures, such as nerves in the back, as is the case in the uterine fibroids HIFU-application, patient can experience pain due to the displacement and pressure on the tissues. A patient or subject is typically provided with a patient emergency alarm, which she or he can press when experiencing pain during a sonication, which in turn aborts the sonication.

When aborting a sonication, some of the intended treatment volume is already heated—simply because the human reaction time is in the 0.5 s range, excluding the effects from mild sedation. In this time, tissue at the focal point can already reach boiling temperatures. Partially sonicated volumes are difficult to re-plan and easily lead to re-sonication of already sonicated tissue. Temperature references need to be re-acquired, which in turn prolong the treatment. Both of these problems can be avoided if the patient detects pain before the actual heating.

A low duty-cycle, high intensity ultrasound pulse train may be used to excite sensitive structures, such as nerves, in the beam path, before the actual heating protocol starts.

When the transducer is in the intended heating position(s), a presonication pulse-train may be executed to mimic the actual sonication. Each pulse may be long enough to cause low-frequency tissue displacement, e.g., 5 ms-10 ms in length. High power levels may be used to induce discernible displacement during the pulse. The focus of the pulse can be optionally de-phased slightly, to reduce heating effects/cavitation at the focal point and to strengthen the displacement effects in the far-field. Pulse train duty-cycle may be kept low to prevent therapeutic heating within the length of the pulse-train and the length of the pulse-train is chosen to allow time for the patient to react, e.g., within 2 seconds. A patient-triggered sonication abort during the presonication pulse-train may reject the intended sonication volume as too risky.

In another embodiment execution of the instructions further causes the processor to control the medical apparatus to switch the focused ultrasonic energy on and off at a duty cycle during the test sonication. If pulsed ultrasound is used during the sonication the duty cycle may be much shorter than the pulse duration used to perform the pulsed ultrasound treatment. This embodiment may be advantageous because pulsing the ultrasound allows the ultrasound to be delivered to the test volume at a reduced average power. The effect of the ultrasound can be tested on the subject without performing a full sonication.

In another embodiment the duty cycle increases during the test sonication. This embodiment may be advantageous because an extremely long duty cycle may be used initially. As the duty cycle increases the power delivered during the test sonication becomes closer to the average power during the sonication. If the duty cycle increases slowly enough this may have the advantage that a subject is able to determine that a sonication point will inflict pain on the subject before tissue damage occurs in the subject.

The duty cycle may in some embodiments increase at a constant rate. In other embodiments the duty cycle may increase as incremental increase. That is to say the increase in the duty cycle may be step like. In another embodiment the increase in the duty cycle increases at a predetermined rate.

In another embodiment the focused ultrasonic energy has a predetermined power level during the sonication of the sonication point.

In another embodiment the test sonication is divided into a first time period and a second time period. During the first time period the test sonication is performed at a reduced power level that is less than the predetermined power level. The reduced power level increases during the first time period. During the second time period the test sonication is performed at the predetermined power level. During the first time period the duty cycle is set to a fixed rate. During the second time period the duty cycle is larger than the fixed rate. During the second time period the duty cycle increases. This embodiment may be advantageous because during the first time period the power is gradually increased. During the second time period the power is at the full power but the duty cycle is gradually increased. This may be advantageous because it allows the subject to more accurately identify if the test sonication point will cause pain when a full powered or normal sonication is performed.

In another embodiment the focused ultrasonic energy has a predetermined power level during the sonication of the sonication point. Execution of the instructions causes the processor to control the medical apparatus to perform the test sonication at a reduced power level that is less than the predetermined power level. The reduced power level is increased during the test sonication. The power level may for instance be increased as at a constant rate of increase. The power level may also be increased incrementally. The power level may also be increased at a predetermined rate. This embodiment may be advantageous because the increasing power level may allow the subject to feel that a test sonication point will cause pain when the full sonication is performed.

In another embodiment execution of the instructions further causes the processor to determine if each of the set of sonication points is a test location by checking if the sonication point is within a selected region indicated within medical image data. The medical image data is descriptive of the anatomy of the subject. This embodiment may be advantageous because a physician or operator may examine a medical image and then select a region adjacent to a sensitive organ or nerve structure. This allows a physician to rapidly identify sonication points which may cause pain when a sonication is performed on a subject.

Execution of the instructions further causes the processor to display the medical image data on a graphical user interface. Execution of the instructions further causes the processor to receive the selection of the selected region from the graphical user interface. For instance a subject may take a mouse and drag a box or other shape over all or a portion of the set of sonication points. This manipulation of the graphical user interface may be used to receive the selection of the selected region.

In another embodiment the medical apparatus further comprises a medical imaging system. A medical imaging system as used herein encompasses any device or apparatus for acquiring medical image data. Execution of the instructions further causes the processor to control the medical apparatus to acquire the medical image data using the medical imaging system. This embodiment is advantageous because the medical apparatus comprises the medical image which is used to acquire the medical image data. This may be beneficial because the instructions may also register the medical image data to the high-intensity focused ultrasound system. This enables physicians or operators to accurately identify regions to be sonicated, receive the selected of the selected region from the graphical user interface, and the medical image may also be used to guide a high-intensity focused ultrasound system during sonication.

In another embodiment the medical imaging system is a magnetic resonance imaging system.

In another embodiment the medical imaging system is a computer tomography system.

In another embodiment the medical imaging system is a diagnostic ultrasound system. The use of the diagnostic ultrasound system may be particularly beneficial because it may be difficult for a physician to identify sensitive structures when performing some sonications when it is guided by a diagnostic ultrasound system.

In another embodiment the high-intensity focused ultrasound system comprises an ultrasonic transducer with an adjustable focus. The focus may be for instance adjusted by mechanically moving elements which comprise the ultrasonic transducer. The ultrasonic transducer may also have an electronic focus. There may be many ultrasonic transducer elements which make up the ultrasonic transducer. A controller or power supply may be able to control the amount of power and/or the phase of alternating electrical current supplied to the ultrasonic transducer. This may allow the shifting of the focus or even the defocusing of the ultrasonic transducer. Execution of the instructions causes the processor to defocus the ultrasonic transducer during the test sonication. This may be beneficial because if the ultrasonic energy is defocused it is less likely to cause tissue damage or necrosis in the subject. It may therefore be beneficial to defocus the ultrasonic transducer during the test sonication. The ultrasonic energy can also be spread over a slightly larger area and it is more likely that the test sonication will stimulate a sensitive region of the subject.

In another embodiment execution of the instructions further causes the processor to remove an additional volume from the treatment volume if the discomfort signal is detected. The additional volume at least partially surrounds the test sonication volume. This embodiment may be beneficial because if a discomfort signal is detected for a particular sonication point then a safety zone around the sonication point may be excluded from sonication. This may result in safer sonication of the treatment volume and may also reduce the amount of time because the additional volume may remove additional sonication points which do not need to be tested. This may increase the throughput of the medical apparatus.

In another embodiment there are multiple test locations. Execution of the instructions causes the processor to control the medical apparatus to perform a test sonication of each of the test locations. This may be beneficial because there may be many regions that may cause discomfort or damage to the subject when sonicated.

In another aspect the invention provides for a computer program product comprising machine executable instructions for execution by a processor controlling a medical apparatus. The medical apparatus comprises a high-intensity focused ultrasound system configured for generating focused ultrasonic energy for sonicating a treatment volume of a subject. The medical apparatus further comprises a signaling device configured to enable the subject to generate a discomfort signal during the sonication of the sonication volume. Execution of the instructions further causes the processor to receive a set of sonication points. The set of sonication points contains coordinates of locations within the treatment volume. At least one of the set of sonication points is identified as a test location. More or all of the set of sonication points may also be a test location.

Execution of the instructions further causes the processor to control the medical apparatus to perform the following for each sonication point of the set of sonication points: determine if a sonication point is the test location, perform a test sonication on the sonication point using the high-intensity focused ultrasound system if the sonication point is the test location, repeatedly test for the discomfort signal from the signaling device during the test sonication, sonicate the sonication point if the sonication point is not a test location or if the signal was not detected, and abort the sonication if the signal was detected. Advantages of this computer program product have been previously discussed in the context of the medical apparatus.

In another aspect the invention provides for a method of operating a medical apparatus. The apparatus comprises a high-intensity focused ultrasound system configured for generating focused ultrasonic energy for sonicating a treatment volume of a subject. The medical apparatus further comprises a signaling device configured to enable the subject to generate a discomfort signal during the sonication of the sonication volume. The method comprises the step of receiving a set of sonication points. The set of sonication points contains coordinates of locations within the treatment volume. At least one of the set of sonication points is identified as a test location. The method further comprises the step of performing the following steps for each of the set of sonication points: determining if the sonication point is the test location, performing a test sonication of the sonication point using the high-intensity focused ultrasound system if the sonication point is the test location, repeatedly testing for the discomfort signal from the signaling device during the test sonication, sonicate the sonication point if the sonication point is not a test location or if the signal is not detected, and aborting the sonication if the signal was detected. The advantages of this method have been discussed in the context of the medical apparatus.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
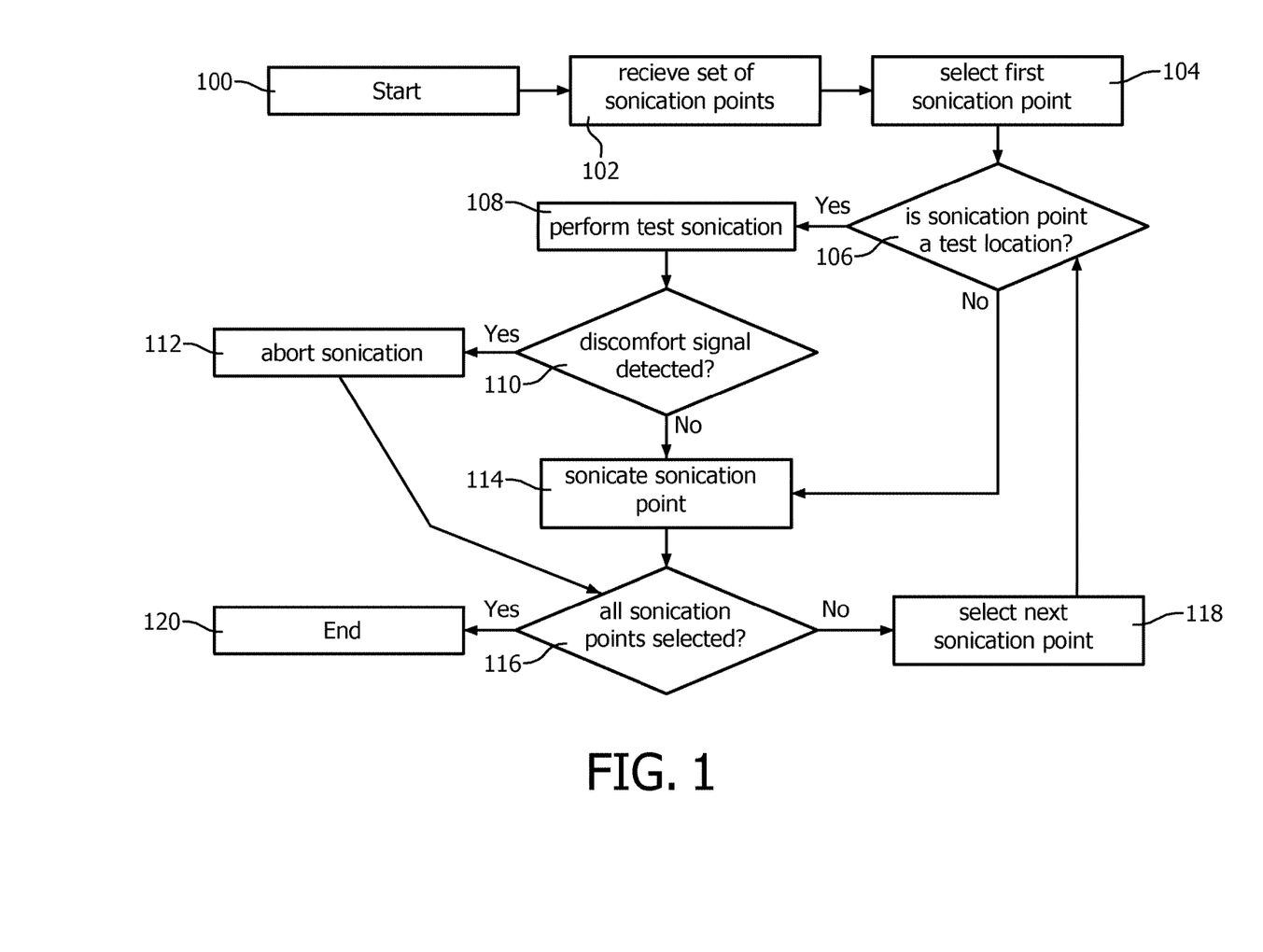
FIG. 1 shows a flow diagram which illustrates a method according to an embodiment of the invention.

FIG. 1 shows a flow diagram which illustrates a method according to an embodiment of the invention. In the first step 100 the method starts. In step 102 a set of sonication points is received. Next in step 104 the first sonication point from the set of sonication points is selected. Next step 106 is a decision box. In step 106 it is determined if the sonication point is a test location. The sonication point may for instance be marked with a flag or Meta data which identifies it as a sonication point. The sonication point may also lie within a selected region or volume which identifies it also as a sonication point. If the sonication point is a test location then a test sonication is performed and box 108 is performed.

If the sonication point is not a test location then the method proceeds to box 114. In this case the sonication point is sonicated. Returning to step 108 after the test sonication is performed it is determined if a discomfort signal was detected in decision box 110. During the performing of test sonication 108 it was repeatedly tested to detect if a discomfort signal was received. If the discomfort signal was detected then box 112 is performed. In box 112 the sonication is aborted. If a discomfort signal was not detected then box 114 is performed. In box 114 again the sonication point is sonicated. After the sonication is aborted or the sonication point is sonicated the method proceeds to step 116. In this box it is determined if all sonication points have been selected. If not then the next sonication point from the set of sonication points is selected and the method returns to step number 106 and this new sonication point is tested to see if it is a sonication point. This loop of the method repeats for all or a subset of the set of sonication points. After all sonication points have been selected the method proceeds to box 120. In box 120, the method ends.

Figure 2:
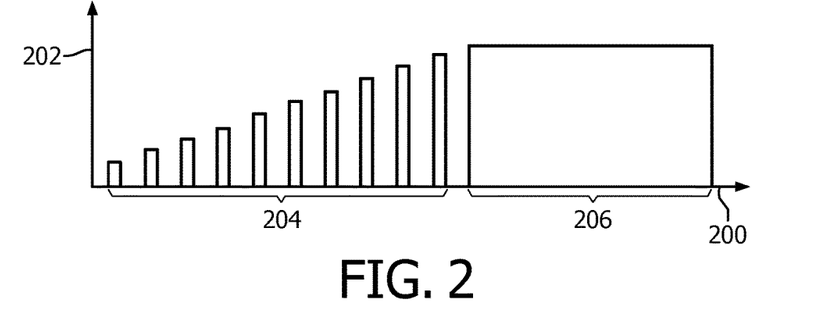
FIG. 2 shows a diagram which illustrates a test sonication and a sonication according to an embodiment of the invention.

FIG. 2 shows a diagram which illustrates a test sonication 204 and a sonication 206. In the graph the x-axis is time and is labeled 200. The y-axis is labeled 202 and represents the ultrasonic power in arbitrary units. The time axis 200 is divided into two periods. The first period is a period where a test sonication 204 is performed and a sonication pulse 206 is performed. The sonication pulse is represented by a solid volume. However it is understood that the ultrasound may be delivered as in a pulsed form. During the test sonication 204 the ultrasound is switched on and off at the duty cycle. Within this duty cycle, the ultrasound may also be pulsed. It is not necessary for it to be continuous. In this example during the test sonication 204 the power is gradually increasing and the ultrasound is switched on and off with a constant duty cycle. In an alternative embodiment the ultrasound is switched with an increasing duty cycle as the time increases.

Figure 3:
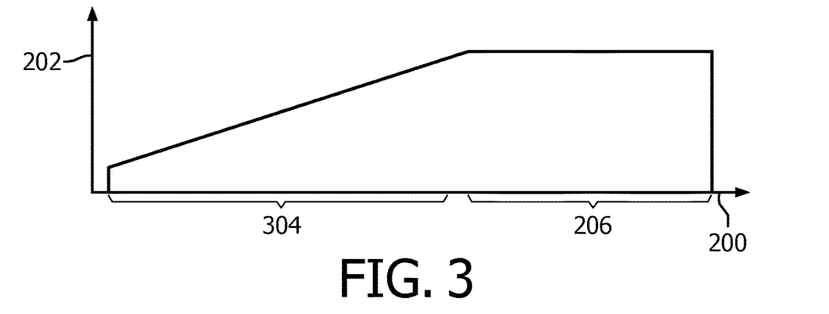
FIG. 3 shows a diagram which illustrates a test sonication and a sonication according to an embodiment of the invention.

FIG. 3 shows a diagram similar to that in FIG. 2. In here in an alternative embodiment a test sonication 304 is performed before the sonication 206. In this case the ultrasonic power 202 is still increasing during the duration of the test sonication 304. However, the sonication is not switched on and off with a duty cycle as was shown in FIG. 2.

Figure 4:
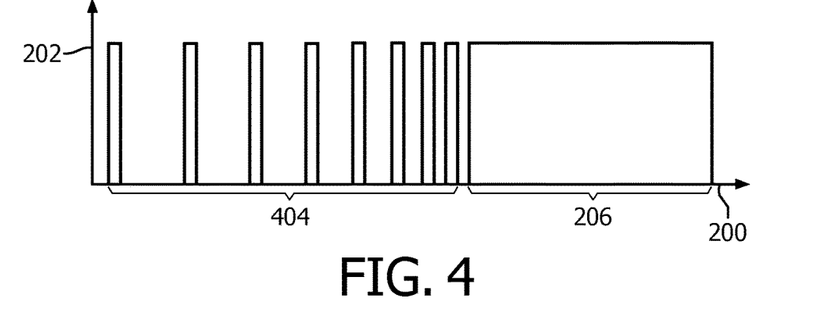
FIG. 4 shows a diagram which illustrates a test sonication and a sonication according to an embodiment of the invention.

FIG. 4 shows an alternative embodiment of a test sonication 404 performed before a sonication 206. In this example during the test sonication the ultrasonic power 202 is held constant and the ultrasonic power 202 is modulated with a gradually increasing duty cycle.

Figure 5:
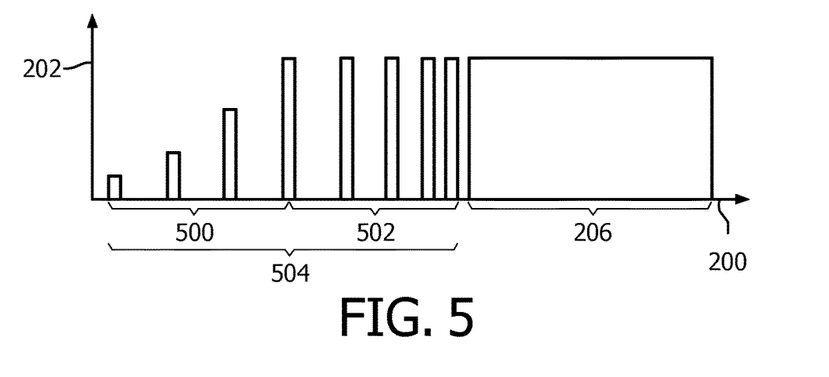
FIG. 5 shows a diagram which illustrates a test sonication and a sonication according to an embodiment of the invention.

FIG. 5 shows a test sonication 504 performed before a sonication 206. In this case the test sonication is divided into a first period 500 and a second period 502. During the first period the ultrasonic power 202 is pulsed at a constant duty cycle but the power level is gradually increased. During the second period 502 the ultrasonic power level 202 is at a constant level. In this case it is the same power level as for the sonication 206. However in some embodiments this power level may be smaller or larger than the power level used during the sonication. The ultrasonic power 202 during the second period 502 is again modulated with a duty cycle. However, during the second period the duty cycle is gradually increasing.

Figure 6:
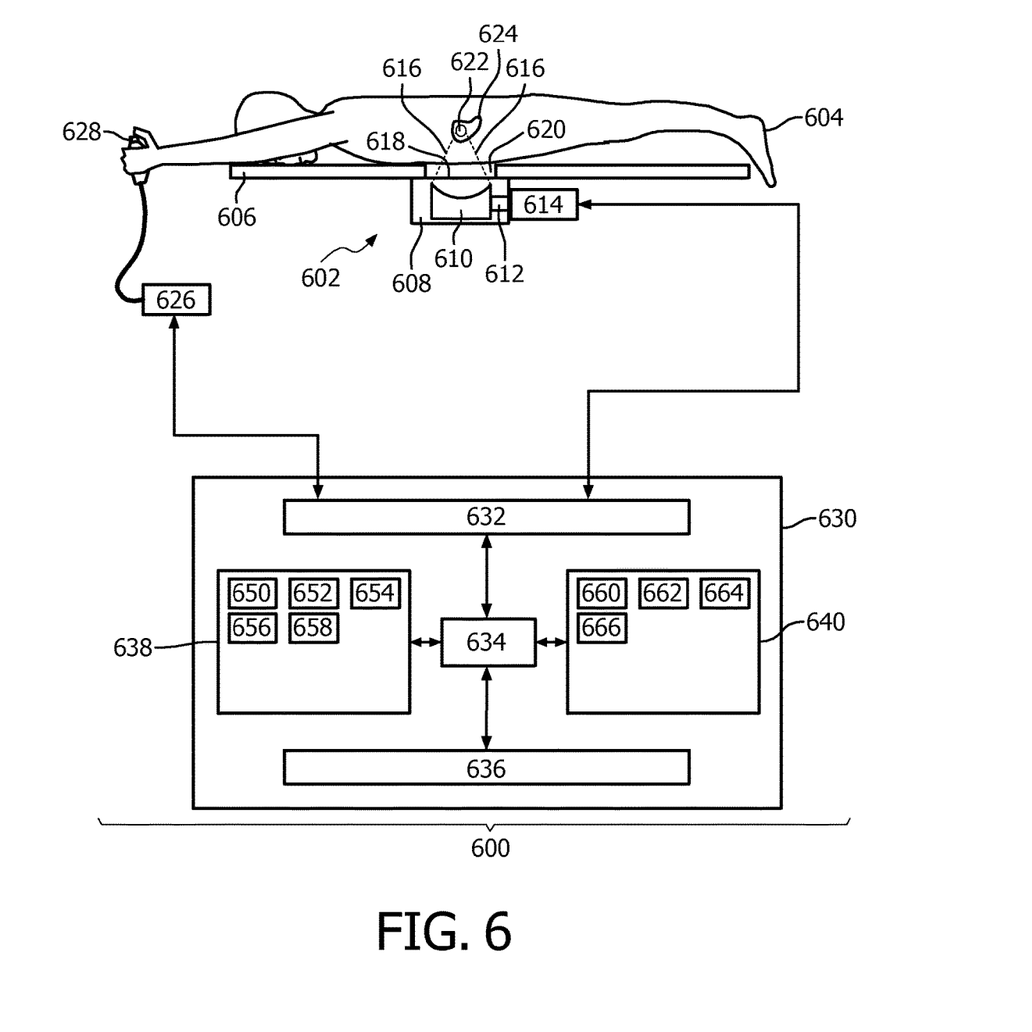
FIG. 6 shows a diagram which illustrates a medical apparatus according to an embodiment of the invention.

FIG. 6 shows a diagram which illustrates a medical apparatus 600 according to an embodiment of the invention. The medical apparatus comprises a high-intensity focused ultrasound system 602. There is a subject 604 reposing on a subject support 606 above the high-intensity focused ultrasound system 602. The high-intensity focused ultrasound system 602 comprises a fluid-filled chamber 608 which houses an ultrasonic transducer 610. The fluid-filled chamber 608 may be filled with a fluid adapted for conducting ultrasound. The ultrasonic transducer 610 is connected to a mechanical positioning system 612 adapted for mechanically positioning the ultrasonic transducer 610. In some embodiments the ultrasonic transducer 610 may comprise multiple transducer elements which may have the phase and/or amplitude of alternating electrical current supplied independently to each transducer element. This allows the focus of the ultrasound to be shifted or adjusted electronically. The mechanical positioning system 612 is connected to an actuator 614 which is adapted for actuating the mechanical positioning system 612. In this way the actuator 614 is able to control the physical position of the ultrasonic transducer 610.

The ultrasound transducer 610 is able to generate ultrasound 616 which travels through the fluid-filled chamber 608. The ultrasound 616 then passes through an ultrasonic window 618. After passing through the ultrasound window 618 the ultrasound in this embodiment passes through a gel pad 620. The gel pad 620 is simply an ultrasonic conducting medium which helps to form an ultrasonic path between the transducer 610 and the subject 604. The ultrasonic energy 616 is then focused to a sonication point 622. The sonication point 622 can be moved either physically and/or electronically to sonicate an entire target zone 624. The medical apparatus 600 further comprises a signaling device 626. The signaling device 626 has a button 628 which is adapted to be pressed by the subject 604. When the subject 604 feels discomfort due to sonication the subject is able to push the button 628. The signaling device 626 and the actuator 614 are shown as being connected to a hardware interface 632 of a computer system 630. The computer 630 further comprises a processor 634 which is connected to the hardware interface, a user interface 636, computer storage 638, and computer memory 640. The processor 634 is able to control the medical apparatus 600 using the hardware interface 632.

Within the computer storage 638 is stored a treatment plan 650. The treatment plan 650 contains data which is descriptive of a treatment of the target zone 624. The treatment plan 650 may for instance contain data on the type and nature of sonication of the target zone 624 and also anatomical structures of the patient 604 which may be used for identifying or locating the target zone 624. The computer storage 638 further contains medical image data that is descriptive of the anatomy of the subject 604. The computer storage 638 further contains image registration 654 of the medical image data 652. The image registration 654 in conjunction with the treatment plan 650 allows the medical apparatus 600 to identify the location of the target zone 624. The computer storage 638 further contains ultrasonic control commands 656. The ultrasonic control commands are commands which are executable by the high-intensity focused ultrasound system 602. Execution of the ultrasonic control commands 656 causes the high-intensity focused ultrasound system 602 to sonicate the target zone 624. The computer storage 638 further contains a set of sonication points 654. The set of sonication points are locations within the subject 604 to be sonicated.

The computer memory 640 contains a control module 660. The control module 660 contains the computer executable code necessary for the processor 634 to control the operation and function of the medical apparatus 600. The computer memory 640 further contains an image registration module 662. The image registration module 662 is able to generate the image registration 654 from the medical image data 652. The computer memory 640 further contains ultrasonic control command generation module 664. The ultrasonic control command generation module 664 uses the image registration 654 and the treatment plan 650 to generate the ultrasonic control commands 656 and/or the set of sonication points 658. The computer memory 640 further contains a discomfort signal detection module 666. The discomfort signal detection module 666 is adapted for detecting the depression of the switch 628 by the subject 604. If the discomfort signal detection module 666 detects a discomfort signal during a test sonication the discomfort signal detection module 666 may abort a particular sonication point or a group of sonication points.

Figure 7:
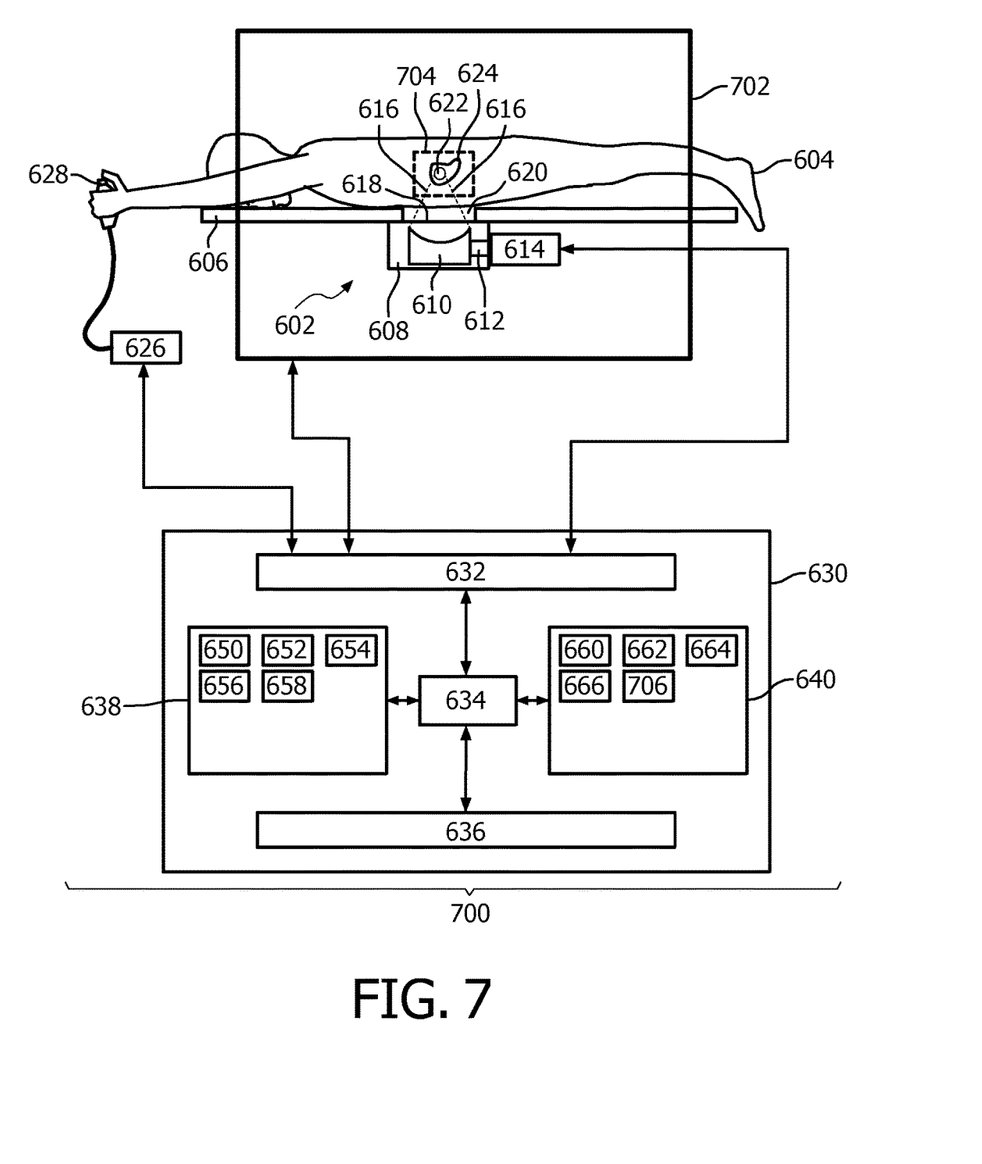
FIG. 7 shows a diagram which illustrates a medical apparatus according to a further embodiment of the invention.

FIG. 7 shows a diagram which illustrates a medical apparatus 700 according to a further embodiment of the invention. The medical apparatus shown in FIG. 7 is in many way equivalent to the medical apparatus 600 shown in FIG. 6. The medical apparatus 700 shown in FIG. 7 however also comprises a medical imaging system 702. The medical imaging system 702 is adapted for acquiring the medical image data 652 from an imaging zone 704. The medical imaging system 702 is representative. It may for instance be, but is not limited to: a magnetic resonance imaging system, a diagnostic ultrasound system, and a computer tomography system. The medical imaging system 702 is also connected to the hardware interface 632. The computer memory 640 contains a medical imaging system control module 706 which allows the processor 634 to control the medical imaging system 702. This enables the medical imaging system 702 to acquire the medical image data 652.

Figure 8:
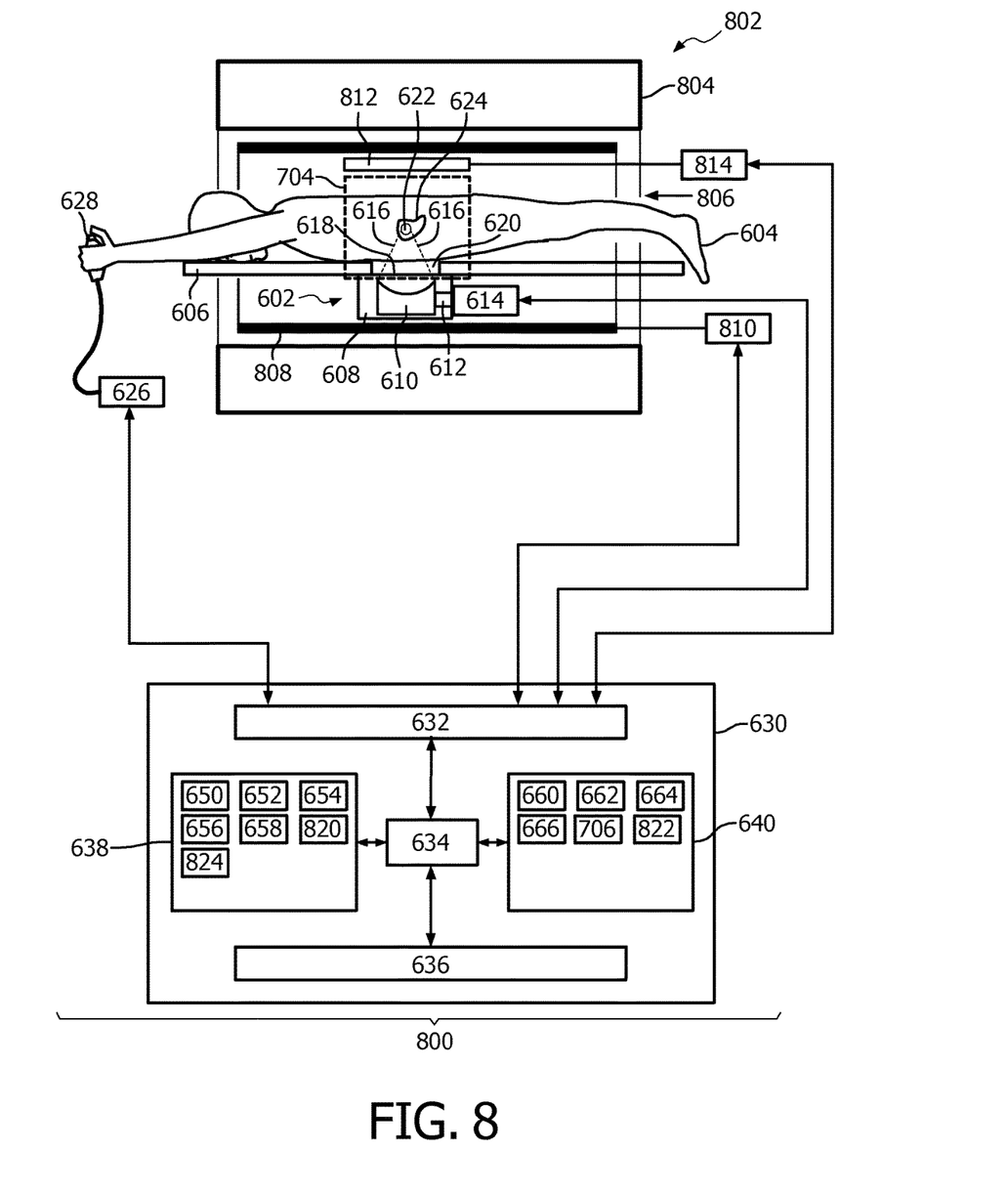
FIG. 8 shows a diagram which illustrates a medical apparatus according to a further embodiment of the invention.

FIG. 8 shows a diagram which illustrates a further embodiment of a medical apparatus 800 according to an embodiment of the invention. This embodiment is in many ways equivalent to the embodiment shown in FIG. 7. However, in this embodiment the medical imaging system 702 of FIG. 7 is a magnetic resonance imaging system 802. The magnetic resonance imaging system 802 comprises a magnet 804. The magnet 804 is a cylindrical type magnet that has a bore 806 through it.

The magnet 804 shown in FIG. 8 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 806 of the cylindrical magnet there is an imaging zone 704 where the magnetic field is strong and uniform enough to perform magnetic resonance imaging.

Within the bore 806 of the magnet there is also a magnetic field gradient coil 808 which is used for acquisition of magnetic resonance data 824 to spatially encode magnetic spins within an imaging zone 704 of the magnet 804. The magnetic field gradient coil is connected to a magnetic field gradient coil power supply 810. The magnetic field gradient coil is intended to be representative. Typically magnetic field gradient coils contain three separate sets of coils for spatially encoding in three orthogonal spatial directions. A magnetic field gradient power supply 810 supplies current to the magnetic field gradient coils. The current supplied to the magnetic field coils is controlled as a function of time and may be ramped or pulsed. The subject 704, the subject support 606 and the high-intensity focused ultrasound system 602 are located within the bore 806 of the magnet 804 also.

Adjacent to the imaging zone 704 is a radio frequency coil 812 for manipulating the orientations of magnetic spins within the imaging zone and for receiving radio transmissions from spins also within the imaging zone 704. The radio frequency coil 812 may contain multiple coil elements. The radio frequency coil 812 may also be referred to as a channel or an antenna. The radio frequency coil 812 is connected to a radio frequency transceiver 814. The radio frequency coil 812 and radio frequency transceiver 814 may be replaced by separate transmit and receive coils and a separate transmitter and receiver. It is understood that the radio frequency coil 812 and the radio frequency transceiver 814 are representative. The radio frequency coil 812 is intended to also represent a dedicated transmit antenna and a dedicated receive antenna. Likewise the radio frequency transceiver 814 may also represent a separate transmitter and receivers.

The computer system 630 in FIGS. 7 and 8 is equivalent to the computer system 630 in FIG. 6. The contents of the computer storage 638 and the computer memory 640 throughout FIGS. 6, 7 and 8 are also equivalent. The computer storage 638 in FIG. 8 is shown as containing a pulse sequence 820. A pulse sequence 820 is a sequence of commands which enable the magnetic resonance imaging system 802 to acquire magnetic resonance data 824. The medical imaging system control module 706 uses the pulse sequence 820 to generate commands which allow the processor 634 to control the magnetic resonance imaging system 802 to acquire the magnetic resonance data 824. An image reconstruction module 822 is then used to construct the magnetic resonance data into magnetic resonance images 652. The magnetic resonance images 652 are an example of medical image data.

Figure 9:
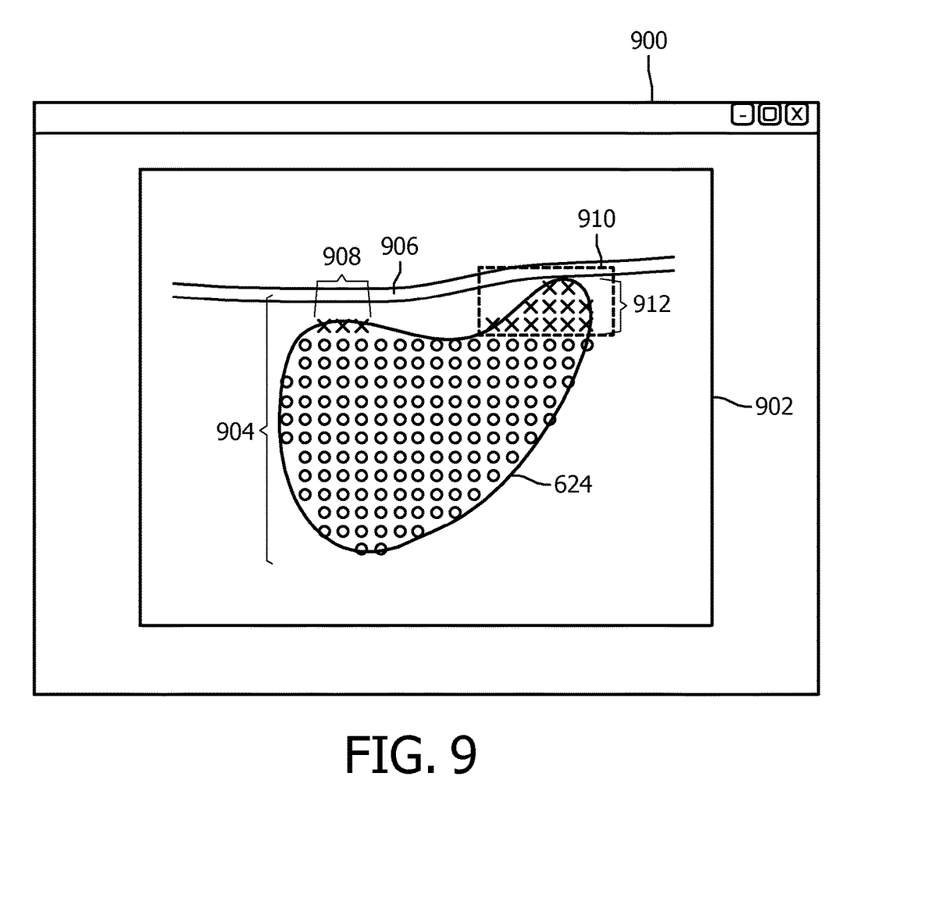
FIG. 9 illustrates a graphical user interface according to an embodiment of the invention.

FIG. 9 shows an example of a graphical user interface 900 according to an embodiment of the invention. In this graphical user interface 900 a medical image 902 is displayed. In this medical image the target zone 624 shown in relation to a sensitive anatomical region 906. The target zone 624 is filled with individual sonication points 904. The sonication points are indicated as "O" shapes or "X" shapes. The "X" shapes are sonication points which are also identified as test locations. Three test locations 908 have been identified in the vicinity of the sensitive anatomical region 906. These for instance may have been indicated as test locations manually using the graphical user interface 900. Shown in the medical image 902 is a selected region 910. The selected region 910 was a region of the medical image 902 that was selected using the graphical user interface 900. All sonication points within the selected region 910 have been identified as test locations 912. The use of identified selected regions allows the rapid selection of sonication points 904 as test locations 912. During the sonication of the target zone 624 each of the sonication points 904 will be sonicated in sequence. The sonication points 904 indicated as test locations 908, 912 have a test sonication performed before the sonication.

Embodiments of the invention may, for example, be used in the applications where the ultrasound beam path crosses nerves at the back, such as in the uterine fibroids or in bone applications. It may also be usable with other applications where the displacement of tissue triggers pain in the patient.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical apparatus comprising:
   a high intensity focused ultrasound system configured to generate focused ultrasonic energy for sonicating a treatment volume of a subject;
   a signaling device configured to enable the subject to generate a discomfort signal during the sonication of the treatment volume;
   a memory containing machine executable instructions;
   a processor for controlling the medical apparatus, wherein execution of the instructions causes the processor to receive a set of sonication points, wherein the set of sonication points contains coordinates of locations within the treatment volume, wherein at least one of the set of sonication points is identified as a test location;
   wherein execution of the instructions causes the processor to control the medical apparatus to perform the following for each sonication point of the set of sonication points:
   determine if the sonication point is the test location;
   perform a test sonication of the sonication point using the high intensity focused ultrasound system if the sonication point is the test location;
   test repeatedly for the discomfort signal from the signaling device during the test sonication;
   sonicate the sonication point if the sonication point is not a test location or if the discomfort signal was not detected; and
   abort the sonication if the discomfort signal was detected.

2. The medical apparatus of claim 1, wherein execution of the instructions further causes the processor to switch the focused ultrasonic energy on and off at a duty cycle during the test sonication.

3. The medical apparatus of claim 2, wherein execution of the instructions further causes the processor to increase the duty cycle during the test sonication.

4. The medical apparatus of claim 3, wherein:
   the focused ultrasonic energy has a predetermined power level during the sonication of the sonication point,
   the test sonication is divided into a first time period and a second time period, and
   execution of the instructions further causes the processor to:
      perform, during the first time period, the test sonication at a reduced power level that is less than the predetermined power level, and increase the reduced power level during the first time period,
      perform, during the second time period, the test sonication at the predetermined power level, and set, during the first time period, the duty cycle to a fixed rate, wherein during the second time period the duty cycle is larger than the fixed rate, and
      increase the duty cycle during the second time period.

5. The medical apparatus of claim 1, wherein the focused ultrasonic energy has a predetermined power level during the sonication of the sonication point, wherein the execution of the instructions causes the processor to perform the test sonication at a reduced power level that is less than the predetermined power level, and wherein the reduced power level is increased during the test sonication.

6. The medical apparatus of claim 1, wherein execution of the instructions further causes the processor to determine if each of the set of sonication points is a test location by checking if the sonication point is within a selected region indicated within medical image data, and wherein the medical image data is descriptive of the anatomy of the subject.

7. The medical apparatus of claim 6, wherein execution of the instructions further causes the processor to:
   display the medical image data on a graphical user interface; and
   receive the selection of the selected region from the graphical user interface.

8. The medical apparatus of claim 7, wherein the medical imaging system is any one of the following: a magnetic resonance imaging system, a computed tomography system, and a diagnostic ultrasound system.

9. The medical apparatus of claim 6, wherein the medical apparatus further comprises a medical imaging system, wherein execution of the instructions further causes the processor to acquire the medical image data using the medical imaging system.

10. The medical apparatus of claim 1, wherein execution of the instructions causes the processor to remove a removal volume from the treatment volume if the discomfort signal is detected, and wherein the removal volume at least partially surrounds the test location.

11. The medical apparatus of claim 1, wherein there are multiple test locations, and wherein execution of the instructions causes the processor to perform a test sonication of each test location.

12. A medical apparatus comprising:
   a high intensity focused ultrasound system comprising an ultrasonic transducer with an adjustable focus, the high intensity focused ultrasound system configured to generate focused ultrasonic energy for sonicating a treatment volume of a subject
   a signaling device configured to enable the subject to generate a discomfort signal during the sonication of the treatment volume;

a memory containing machine executable instructions;
a processor for controlling the medical apparatus, wherein execution of the instructions causes the processor to receive a set of sonication points, wherein the set of sonication points contains coordinates of locations within the treatment volume, wherein at least one of the set of sonication points is identified as a test location;
wherein execution of the instructions causes the processor to control the medical apparatus to perform the following for each sonication point of the set of sonication points:
determine if the sonication point is the test location;
perform a test sonication of the sonication point using the high intensity focused ultrasound system and defocus the ultrasonic transducer if the sonication point is the test location;
test repeatedly for the discomfort signal from the signaling device during the test sonication;
sonicate the sonication point if the sonication point is not a test location or if the discomfort signal was not detected; and
abort the sonication if the discomfort signal was detected.

13. A non-transitory computer program product comprising machine executable instructions for execution by a processor controlling a medical apparatus, wherein the medical apparatus comprises a high intensity focused ultrasound system configured for generating focused ultrasonic energy for sonicating a treatment volume of a subject, wherein the medical apparatus further comprises a signaling device configured to enable the subject to generate a discomfort signal during the sonication of the treatment volume, wherein execution of the instructions causes the processor to receive a set of sonication points, wherein the set of sonication points contains coordinates of locations within the treatment volume, wherein at least one of the set of sonication points is identified as a test location;
wherein execution of the instructions causes the processor to control the medical apparatus to perform the following for each sonication point of the set of sonication points:
determine if the sonication point is the test location;
perform a test sonication of the sonication point using the high intensity focused ultrasound system if the sonication point is the test location;
test repeatedly for the discomfort signal from the signaling device during the test sonication;
sonicate the sonication point if the sonication point is not a test location or if the discomfort signal was not detected; and
abort the sonication if the discomfort signal was detected.

14. The non-transitory computer program product of claim 13, wherein execution of the instructions further causes the processor to:
switch the focused ultrasonic energy on and off at a duty cycle during the test sonication; and
increase the duty cycle during the test sonication.

15. The non-transitory computer program product of claim 13, wherein the high intensity focused ultrasound system comprises an ultrasonic transducer with an adjustable focus, wherein execution of the instructions further causes the processor to defocus the ultrasonic transducer during the test sonication.

16. A method of operating a medical apparatus, wherein the apparatus comprises a high intensity focused ultrasound system configured for generating focused ultrasonic energy for sonicating a treatment volume of a subject, wherein the medical apparatus further comprises a signaling device configured to enable the subject to generate a discomfort signal during the sonication of the treatment volume, wherein the method comprises the steps of receiving a set of sonication points, wherein the set of sonication points contains coordinates of locations within the treatment volume, wherein at least one of the set of sonication points is identified as a test location, wherein the method further comprises the step of performing the following steps for each of the set of sonication points:
determining if the sonication point is the test location;
in response to the sonication point being the test location, performing a test sonication of the sonication point using the high intensity focused ultrasound system;
testing repeatedly for the discomfort signal from the signaling device during the test sonication;
in response to the sonication point not being the test location or in response to the discomfort signal not being detected, sonicating the sonication point; and
in response to detecting the discomfort signal, aborting the sonication.

17. The method of claim 16, further comprising:
during the test sonication, switch the focused ultrasonic energy on and off at a duty cycle; and
increase the duty cycle during the test sonication.

18. The method of claim 16, wherein:
the high intensity focused ultrasound system comprises an ultrasonic transducer with an adjustable focus; and
the method further comprises defocusing the ultrasonic transducer during the test sonication.

* * * * *